United States Patent
Klenk et al.

(10) Patent No.: US 9,239,320 B2
(45) Date of Patent: Jan. 19, 2016

(54) METHOD FOR VERIFYING THE PLAUSIBILITY OF A MEASURING DEVICE FOR DETERMINING THE QUALITY OF AN AQUEOUS UREA SOLUTION IN A RESERVOIR OF AN SCR CATALYST SYSTEM

(71) Applicant: Robert Bosch GmbH, Stuttgart (DE)

(72) Inventors: Wolfgang Klenk, Loechgau (DE); Matthias Burger, Murr (DE); Reinold Weinmann, Esslingen am Neckar (DE); Wilhelm Dueck, Niefern (DE)

(73) Assignee: Robert Bosch GmbH, Stuttgart (DE)

( * ) Notice: Subject to any disclaimer, the term of this patent is extended or adjusted under 35 U.S.C. 154(b) by 351 days.

(21) Appl. No.: 13/907,643

(22) Filed: May 31, 2013

(65) Prior Publication Data

US 2013/0319070 A1 Dec. 5, 2013

(30) Foreign Application Priority Data

May 31, 2012 (DE) .......................... 10 2012 209 240

(51) Int. Cl.
| | |
|---|---|
| *G01N 33/00* | (2006.01) |
| *F01N 3/20* | (2006.01) |
| *F01N 11/00* | (2006.01) |
| *F01N 3/04* | (2006.01) |

(52) U.S. Cl.
CPC .............. *G01N 33/00* (2013.01); *F01N 3/2066* (2013.01); *F01N 11/00* (2013.01); *F01N 2550/05* (2013.01); *F01N 2610/02* (2013.01); *F01N 2610/142* (2013.01); *F01N 2610/148* (2013.01); *F01N 2900/0412* (2013.01); *F01N 2900/0416* (2013.01); *F01N 2900/1814* (2013.01); *F01N 2900/1818* (2013.01); *Y02T 10/24* (2013.01); *Y02T 10/47* (2013.01)

(58) Field of Classification Search
CPC .... G01N 31/10; G01N 33/00; F01N 2610/02; F01N 2610/148; F01N 2900/0412; F01N 2900/0416; F01N 2900/1814; F01N 2900/1818
USPC ...................................... 73/1.02, 865.8–865.9
See application file for complete search history.

(56) References Cited

U.S. PATENT DOCUMENTS

| | | | |
|---|---|---|---|
| 2006/0163250 A1 * | 7/2006 | Colavita ................... | 220/203.28 |
| 2007/0209428 A1 * | 9/2007 | Nishina et al. ............... | 73/61.76 |
| 2007/0283685 A1 | 12/2007 | Ripper et al. | |
| 2012/0118059 A1 * | 5/2012 | Reimer et al. .............. | 73/290 V |

FOREIGN PATENT DOCUMENTS

| | | | |
|---|---|---|---|
| DE | 10139142 | | 2/2003 |
| JP | 2011179360 A | * | 9/2011 |
| WO | 2006051017 | | 5/2006 |

* cited by examiner

*Primary Examiner* — Eric S McCall
*Assistant Examiner* — Anthony W Megna Fuentes
(74) *Attorney, Agent, or Firm* — Michael Best & Friedrich LLP

(57) ABSTRACT

A method for verifying the plausibility of a measuring device for determining a quality of an aqueous urea solution in a reservoir of an SCR catalyst system comprises determining whether a filling of the reservoir has taken place, determining the quality of the aqueous urea solution in the reservoir and detecting whether an error of the measuring device is present or whether the reservoir was filled with an aqueous urea solution, the quality of which deviates from a default value consisting of a filling status of the reservoir and the quality of the aqueous urea solution in said reservoir.

20 Claims, 2 Drawing Sheets

METHOD FOR VERIFYING THE PLAUSIBILITY OF A MEASURING DEVICE FOR DETERMINING THE QUALITY OF AN AQUEOUS UREA SOLUTION IN A RESERVOIR OF AN SCR CATALYST SYSTEM

BACKGROUND OF THE INVENTION

The present invention relates to a method for verifying the plausibility of a measuring device for determining a quality of a urea aqueous solution in a reservoir of an SCR catalyst system. In addition, the present invention relates to a computer program which executes all steps of the inventive method if said method is run in a computing device or control device. Finally the present invention relates to a computer program product comprising a program code, which is stored on a machine-readable carrier, for carrying out the inventive method if the program is executed on a computer or in a control device.

In order to comply with increasingly stringent exhaust emission legislation, it is necessary to reduce nitrogen dioxides in the exhaust gas of internal combustion engines, in particular diesel engines. To this end, it is known to dispose an SCR catalyst (selective catalytic reduction) in the exhaust gas region of internal combustion engines, said catalyst reducing nitrogen oxides ($NO_x$) contained in the exhaust gas of an internal combustion engine to nitrogen in the presence of a reducing agent. The proportion of nitrogen oxide in the exhaust gas can thereby be considerably reduced. Ammonia ($NH_3$), which is added to the exhaust gas, is required for the course of the reaction. For that reason, $NH_3$ or $NH_3$-releasing reagents are used as the reducing agent. As a rule, a hydrous urea solution (aqueous urea solution) is used which is injected into the exhaust gas tract upstream of the SCR catalyst. Ammonia forms from this solution which acts as reducing agent. A 32.5% aqueous urea solution is commercially available under the brand name AdBlue®.

In the case of commercial vehicles, the aqueous urea solution is refilled by the driver. A refilling of the reagent by the driver, which occurs outside of specified maintenance intervals, is also being discussed for passenger vehicles in the future. A check as to whether the refilled substance actually conforms to aqueous urea solutions or, respectively, as to whether the urea concentration in the aqueous urea solution corresponds to the relevant ISO standard 22241 or to the DIN standard 70070 has not occurred to date. The lawmakers will, however, demand in the future that a check is immediately made to detect whether an attempt to defraud was made when refilling the aqueous urea solution and that corresponding measures, such as, for example, a restriction of engine start-up or a reduction in engine performance, can be introduced if fraud were detected. For this purpose, the systems will have to be expanded to include a quality sensor which determines the quality of the aqueous urea solution. An SCR system comprising such a quality sensor is known, for example, from the German patent application DE 101 39 142 A1. This document does not, however, describe how a malfunction of the quality sensor can be detected in order to prevent an erroneous detection of a deviating aqueous urea solution or a filling of the reservoir with a substance which does not have the properties of an aqueous urea solution.

SUMMARY OF THE INVENTION

The inventive method for verifying the plausibility of a measuring device for determining a quality of an aqueous urea solution in a reservoir of an SCR catalyst system, i.e. a quality sensor, consists of determining whether a filling of the reservoir has taken place. The quality of the urea solution in the reservoir is determined and a check is then made to see whether an error due to a faulty measuring device is present or whether the reservoir was filled with an aqueous urea solution, the quality of which deviates from a default value, by a fill status of the reservoir and the quality of the aqueous urea solution in the reservoir being evaluated. According to the invention, the quality sensor can be disposed in the reservoir. Said sensor can however also alternatively be disposed in a line, through which the aqueous urea solution is transported on its way to the SCR catalyst, for example in the line of a delivery module.

The inventive method then preferably detects that the reservoir was filled with an aqueous urea solution, the quality of which deviates from a predetermined value if a filling of the reservoir has taken place and if the measuring device for determining a quality of the aqueous urea solution determines that the concentration of said aqueous urea solution deviates from a predetermined value, said aqueous urea solution is contaminated and/or the contents of the reservoir do not relate to an aqueous urea solution.

It is furthermore preferred that the signal of the measuring device is then detected to be implausible if a filling of the reservoir has not taken place or if the measuring device for determining a quality of the aqueous urea solution determines that the concentration of said aqueous urea solution exceeds a predetermined value, said aqueous urea solution is contaminated and/or the contents of the reservoir do not relate to an aqueous urea solution.

In addition, it is preferred that the fact an error of the measuring device could be present is detected if a filling of the reservoir has not taken place and if the measuring device for determining a quality of an aqueous urea solution determines that the concentration of the aqueous urea solution exceeds a predetermined value. In this case, it is, however, also possible that an ageing of said aqueous urea solution has occurred. OBD legislation is then applicable, i.e., the aqueous urea solution has to be replaced if the concentration thereof further decreases. This is especially true if the concentration is too small to adhere to the OBD limit value.

The predetermined value for the concentration of the aqueous urea solution relates particularly to a concentration in the range of 26.5% by weight to 33.5% by weight. This range covers inter alia the admissible concentration of AdBlue® according to the ISO standard 22241 or to the DIN standard 70070.

Whether a filling of the reservoir has taken place can, for example, be determined via a fill level sensor in the reservoir. The signal of the fill level sensor is preferably evaluated in the reservoir in order to furthermore eliminate the possibility of an attempt to defraud with regard to the filling process, for example by means of a slow refilling. In a particularly preferential manner, the signal of the fill level sensor is checked for plausibility against an amount of aqueous urea solution metered into the SCR catalyst. A further alternative preferred according to the invention to determine whether a filling of the reservoir has taken place, which excludes the possibility of manipulation occurring thereby, consists of checking whether a cover of the reservoir has been opened.

The inventive method can be implemented in an SCR catalytic system comprising a quality sensor without structural changes having to be performed thereon. The inventive computer program, which executes all steps of the inventive method, serves to meet this end if it is run in a computing device or control device. The inventive computer program product comprising a program code, which is stored on a machine-readable carrier, serves to implement the inventive method if the program is executed on a computer or in a control device.

BRIEF DESCRIPTION OF THE DRAWINGS

Exemplary embodiments of the invention are depicted in the drawings and explained in detail in the following description.

DETAILED DESCRIPTION

Figure 1:
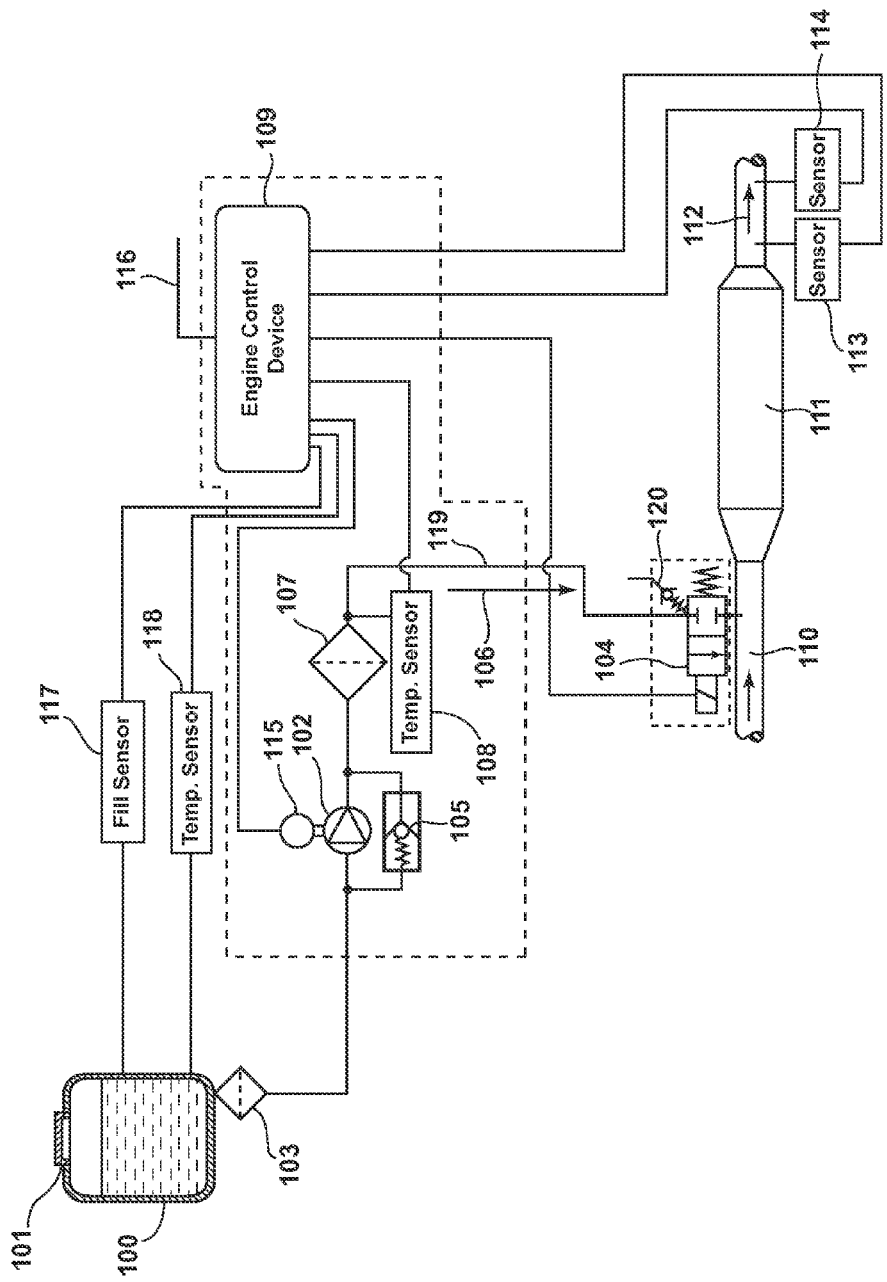
FIG. 1 shows an SCR catalyst system comprising a quality sensor according to prior art.

An SCR catalyst system according to the WIPO patent application WO 2006/051017 A1, in which the inventive method can be carried out, is depicted in FIG. 1. An aqueous urea solution is stored in a reservoir 100 comprising a cover 101 as reducing agent for the exhaust gas aftertreatment for purifying an exhaust gas of a combustion engine of a motor vehicle, which aqueous urea solution can be introduced into a metering valve 104 via a delivery pump 102 and an unspecified line as well as a prefilter 103. The urea solution is coarsely filtered in the prefilter 103. The delivery pump 102 can be circumvented with a bypass valve 105, which in the case of excessive pressure opens in a normal operation-delivery direction 106 downstream of the delivery pump 102. The delivery pump 102 conveys the aqueous urea solution to the metering valve 104 in the normal operation-delivery direction 106 designated by an arrow, said metering valve directly metering the urea solution into an exhaust gas tract without air support for forming aerosols. A filter 107, with which the urea solution is purified before it arrives at the metering valve, is disposed downstream of the delivery pump 102. A sensor 108 for determining the temperature of the urea solution is disposed downstream of the filter 107, the former being connected via an unspecified signal line to an engine control device 109. In order to purify the exhaust gas, the urea solution is introduced at a metering point into an exhaust gas inlet region 110 of an SCR catalyst 111. An exhaust gas flow direction at the exhaust gas inlet region 110 and at the exhaust gas outlet region 112 is designated in each case by arrows. Conventional sensors 113, 114 are provided at the exhaust gas outlet region 112, for example pressure sensors, temperature sensors, lambda probes, NOx sensors and the like, which are connected via unspecified signal lines to the control device 109 and are constituent parts of a conventional exhaust gas aftertreatment system. Independently of operating parameters and/or operating states, said control device 109 furthermore controls the metering valve 104 as well as the delivery pump 102 or, respectively, the drive motor 115 thereof via unspecified signal lines. In addition, said control device 109 is connected via a CAN bus 116 to the combustion engine of the motor vehicle. A sensor 117 for measuring the fill level as well as a sensor 118 for measuring the reservoir temperature is provided at the reservoir 100, said sensors being connected to the control device 109 via unspecified data lines. The metering valve 104 can be operated in a pulse-width modulated manner. When the engine of the vehicle is switched off, said metering valve 104 or a region 119 of a delivery line between the delivery pump 102 and said metering valve 104 can be drained in the opposite direction of the normal operation-delivery direction 106, wherein the delivery direction of the delivery pump 102 is reversed and the urea solution is conveyed back into the reservoir 100 against the normal operation-delivery direction 106, which prevails during normal operation. A ventilation valve 120 disposed upstream of said metering valve 104 is opened and said metering valve 104 is closed. A suction of exhaust gas and particles out of the SCR catalytic converter 111 and the exhaust gas inlet region 110 is prevented by means of a gas flow, for example by means of a supply of fresh air, through the ventilation valve 120. If the region 119 has been emptied, said metering valve 104 can be opened towards the exhaust gas tract in order to drain a small residual amount of the urea solution from the metering valve itself 104.

Figure 2:
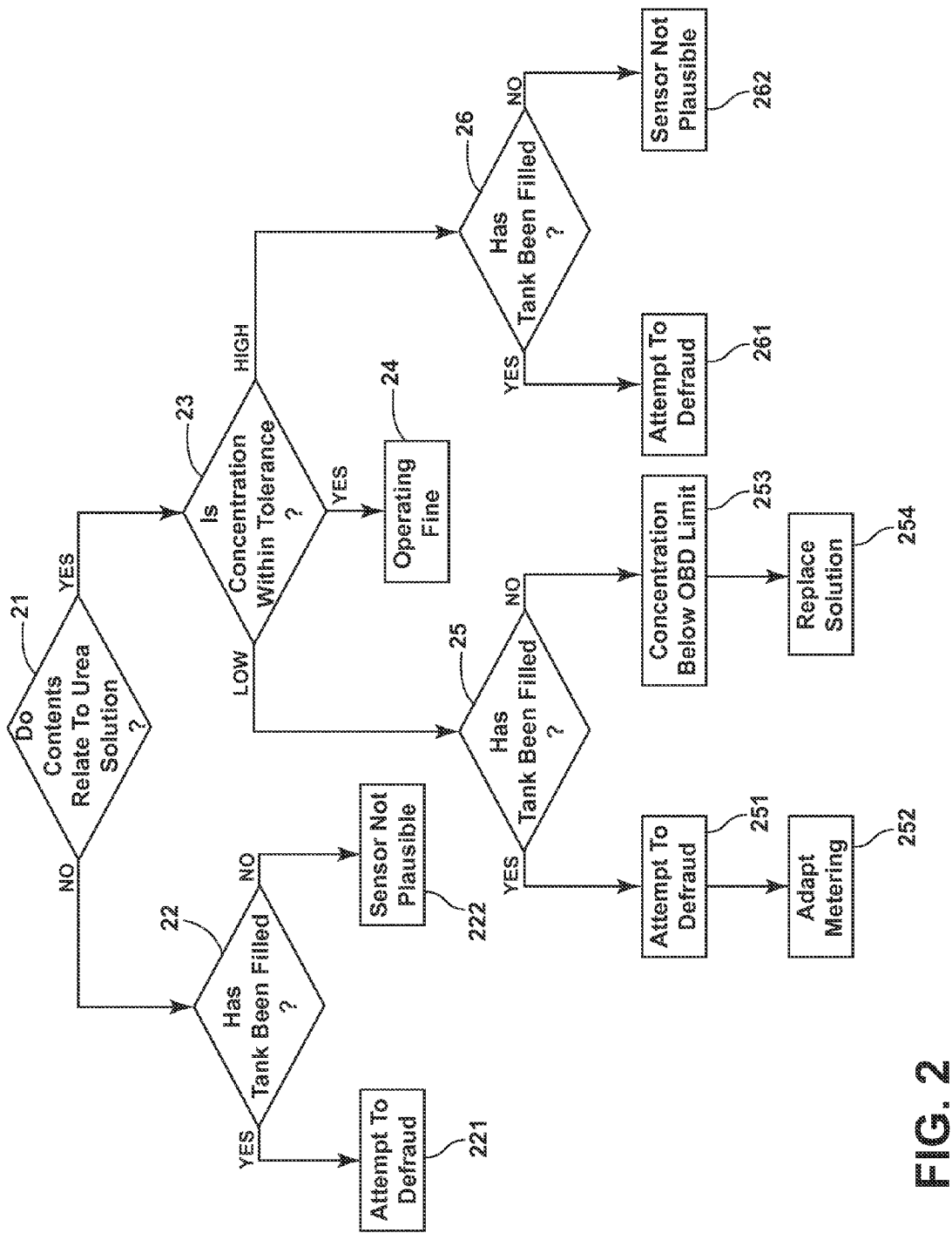
FIG. 2 is a schematic depiction of a method according to one embodiment of the invention.

In one embodiment of the inventive method, a determination is made by means of interaction of a quality sensor with the reducing agent tank 110 whether the aqueous urea solution is contaminated or if the liquid in the reducing agent tank 110 even relates to an aqueous urea solution. In addition, the concentration of the aqueous urea solution is determined. Such a quality sensor is not contained in the SCR catalyst system according to the WIPO patent application WO 2006/051017 and is not depicted in FIG. 1. Said quality sensor must be added to this system in order to carry out the inventive method therein. It is determined from the signal of the fill level sensor 117 if a filling of the reducing agent tank 100 has taken place. FIG. 2 shows a flow diagram of the inventive method pursuant to this embodiment. An assessment is made in a procedural step 21 whether the contents of the reducing agent tank 100 relate to an aqueous urea solution. If this is not the case, a decision is made in a procedural step 22 whether a filling of the reducing agent tank 100 has taken place. In the event that a filling has occurred, an attempt to defraud is detected in step 221. Otherwise it is detected in step 222 that the signal of the quality sensor is not plausible. In this case, the quality sensor must be checked, observed or replaced.

Provided that the contents of the reducing agent tank 100 relate to an aqueous urea solution, the concentration thereof is compared to the concentration of 32.5% by weight, which conforms to the standards, in step 23. If the concentration of the aqueous urea solution corresponds to the default value within the error tolerance of the quality sensor, it is recognized in step 24 that interventions into the SCR catalyst system, as, for example, an adaptation of the metering strategy of the SCR catalyst 111, are not necessary. If the concentration lies below the default value, a decision is made in step 25 whether a filling of the reducing agent tank 100 has taken place. If said tank has been filled, an attempt to defraud is detected in step 251. In addition, the metering strategy of the SCR catalyst 111 is adapted in step 252. If a filling did not take place, the method recognizes that an ageing of the aqueous urea solution has possibly occurred and a check is made in step 253 as to whether the concentration of the aqueous urea solution lies below the concentration, which is necessary to adhere to the OBD limit value. In the event that it is indicated that the concentration is indeed below said OBD limit value, recognition is made in step 254 that the aqueous urea solution has to be replaced. It is, however, also possible that an error of the quality sensor is present. Steps 253 and 254 can be dispensed with if a quality sensor is used which is capable not only of determining the urea concentration of the aqueous urea solution but also the ammonia content thereof.

In the event that the concentration of the aqueous urea solution lies above the default value, a decision is then made in step 26 as to whether a filling of the reducing agent tank has taken place. If such a filling took place, an attempt to defraud is detected in step 261. It can be assumed that that the aqueous urea solution does not relate to AdBlue® but to a self-mixture, for example a mixture of fertilizer and water. Otherwise it is recognized in step 262 that the signal of the quality sensor is not plausible.

What is claimed is:

1. A method for verifying the plausibility of a measuring device for determining a quality of an aqueous urea solution in a reservoir (100) of an SCR catalyst system, the method comprising:
   determining whether contents of the reservoir relate to an aqueous urea solution,
   determining whether a filling of the reservoir has taken place,
   detecting an error of the measuring device is present when contents of the reservoir do not relate to an aqueous urea solution and the reservoir was not filled, and
   when the contents of the reservoir relate to an aqueous urea solution, determining whether the quality of the aqueous urea solution in the reservoir deviates from a predetermined value.

2. The method according to claim 1, wherein when the method recognizes that the contents of the reservoir relate to the aqueous urea solution, determining whether the quality of the aqueous urea solution deviates from a predetermined value, includes the measuring device determining that at least one of
   a concentration of the aqueous urea solution deviates from the predetermined value, and
   the aqueous urea solution is contaminated.

3. The method according to claim 1, wherein the method recognizes that a signal of the measuring device is not plausible when a filling of the reservoir has not taken place and the measuring device for detecting a quality of the aqueous urea solution determines that at least one of
   a concentration of the aqueous urea solution exceeds the predetermined value, and
   the aqueous urea solution is contaminated.

4. The method according to claim 1, wherein the method recognizes that an error of the measuring device could be present when a filling of the reservoir has not taken place and when the measuring device for detecting a quality of the aqueous urea solution determines that a concentration of said aqueous urea solution falls below a predetermined value.

5. The method according to claim 2, wherein the predetermined value for the concentration of the aqueous urea solution is from about 26.5% by weight to about 33.5% by weight.

6. The method according to claim 1, wherein the method determines whether a filling of the reservoir has taken place by a signal of a fill level sensor in the reservoir being evaluated.

7. The method according to claim 6, wherein the method determines whether a filling of the reservoir has taken place by the signal of the fill level sensor being checked for plausibility against an amount of aqueous urea solution metered into the SCR catalyst.

8. The method according to claim 1, wherein the method determines whether a filling of the reservoir has taken place by checking whether a cover of the reservoir has been opened.

9. A computer program, which executes all steps of a method according to claim 1 when the program is executed by a computer or by a control device.

10. The computer program product comprising a program code, which is stored on a machine-readable carrier, for carrying out the method according to claim 1 when the program is executed by a computer or by a control device.

11. A method for verifying plausibility of a measuring device provided for determining a quality of an aqueous urea solution in a reservoir of an SCR catalyst system, the method comprising:
    determining whether content of fluid in the reservoir is related to an aqueous urea solution; and
    when the content of fluid in the reservoir is not related to the aqueous urea solution, determining whether the reservoir has been filled, and if the reservoir has not been filled providing an indication that the measuring device is not plausible.

12. The method according to claim 11, including the measuring device determining concentration of the aqueous urea solution, and
    when the concentration of the aqueous urea solution is greater than a predetermined value and the reservoir has not been filled, providing an indication that the measuring device is not plausible.

13. The method according to claim 12, including detecting ammonia content with the measuring device.

14. The method according to claim 12, including when the concentration of the aqueous urea solution is within the predetermined value, the SCR catalyst system operates without interventions.

15. The method according to claim 12, wherein the predetermined value represents a concentration from about 26.5% by weight to about 33.5% by weight.

16. The method according to claim 11, wherein the said method determines whether a filling of the reservoir has taken place by the signal of the fill level sensor being checked for plausibility against an amount of aqueous urea solution metered into the SCR catalyst.

17. The method according to claim 16, including the measuring device determining concentration of the aqueous urea solution, and
    when the concentration of the aqueous urea solution is greater than a predetermined value and the reservoir has not been filled, providing an indication that the measuring device is not plausible.

18. A method for verifying plausibility of a measuring device provided for determining a quality of an aqueous urea solution in a reservoir of an SCR catalyst system, the method comprising:
    determining whether content of fluid in the reservoir is related to an aqueous urea solution;
    when the content of fluid in the reservoir is not related to an aqueous urea solution, determining whether the reservoir has been filled,
    when the reservoir has not been filled providing an indication that the measuring device is not plausible,
    when the reservoir has been filled, indicating an attempt to defraud by not filling with an aqueous urea solution.

19. The method according to claim 18, including when the content of fluid in the reservoir is related to an aqueous urea solution,
    detecting a concentration of urea solution and comparing with a predetermined value,
    when the detected concentration is greater than the predetermined value and the reservoir has not been filled, providing an indication that a quality sensor is not operating properly,
    when the detected concentration is greater than the predetermined value and the reservoir has been filled, indicating an attempt to defraud by not filling with an aqueous urea solution, when the detected concentration is less than the predetermined value and the reservoir has not been filled, and the concentration is below OBD limit, providing an indication that a quality sensor is not operating properly, when the detected concentration is less than the predetermined value and the reservoir has been filled, indicating an attempt to defraud and adapting a metering strategy.

20. The method according to claim 19, including determining whether a filling of the reservoir has taken place by a signal of a fill level sensor, the signal of the fill level sensor being checked for plausibility against an amount of aqueous urea solution metered into the SCR catalyst.

* * * * *